United States Patent

Licht et al.

[11] Patent Number: 6,162,466
[45] Date of Patent: Dec. 19, 2000

[54] SUSTAINED RELEASE FORMULATION OF CARBAMAZEPINE

[75] Inventors: Daniela Licht, Givat Shmuel; Marina Zholkoysky, Bat Yam; Roman Kaplan, Holon; Michael Friedman, Jerusalem, all of Israel; Abraham Yacobi, New City, N.Y.; Yechiel Golander, Herzlia, Israel; Dan Moros, Larchmont; Barrie Levitt, Mamaroneck, both of N.Y.

[73] Assignee: Taro Pharmaceutical Industries Ltd., Herzlia, Israel

[21] Appl. No.: 09/292,609

[22] Filed: Apr. 15, 1999

[51] Int. Cl.[7] .................................. A61K 9/26; A61K 9/32
[52] U.S. Cl. .......................... 424/468; 424/469; 424/470; 424/475; 424/482; 514/777; 514/778; 514/781; 514/784; 514/960
[58] Field of Search ..................... 424/468, 469, 424/470, 465, 475, 482

[56] References Cited

FOREIGN PATENT DOCUMENTS 44 23 078 A1  4/1996  Germany.
94-298499  1/1994  Japan.

OTHER PUBLICATIONS

Bialer et al, "Criteria to Assess In Vivo Performance and Bioequivalence of Generic Controlled–Release Formulations of Carbamazepine", *Epilepsia*, 39(5): 513–519, 1998.

"Aqueous Polymeric Coatings for Pharaceutical Dosage Forms", ed. McGinity, JW, 2nd Ed., pp. 9–15, 55, 65, 73–81, 109–, 133, 169–189, 1992.

*Primary Examiner*—James M. Spear
*Attorney, Agent, or Firm*—Mark M. Friedman

[57] ABSTRACT

The present invention provides a pharmaceutical preparation in tablet form, where the active ingredient is an anti-epileptic medication, preferably a sustained release formulation, and most preferably a sustained release formulation where the active ingredient is carbamazepine. The product consists of carbamazepine particles coated with a single hydrophobic layer and is in a disintegrating tablet form.

22 Claims, 5 Drawing Sheets

Dissolution (%) of Carbamazepine (CMZ) tablets, 200 mg. 1% SLS, app. USP 2

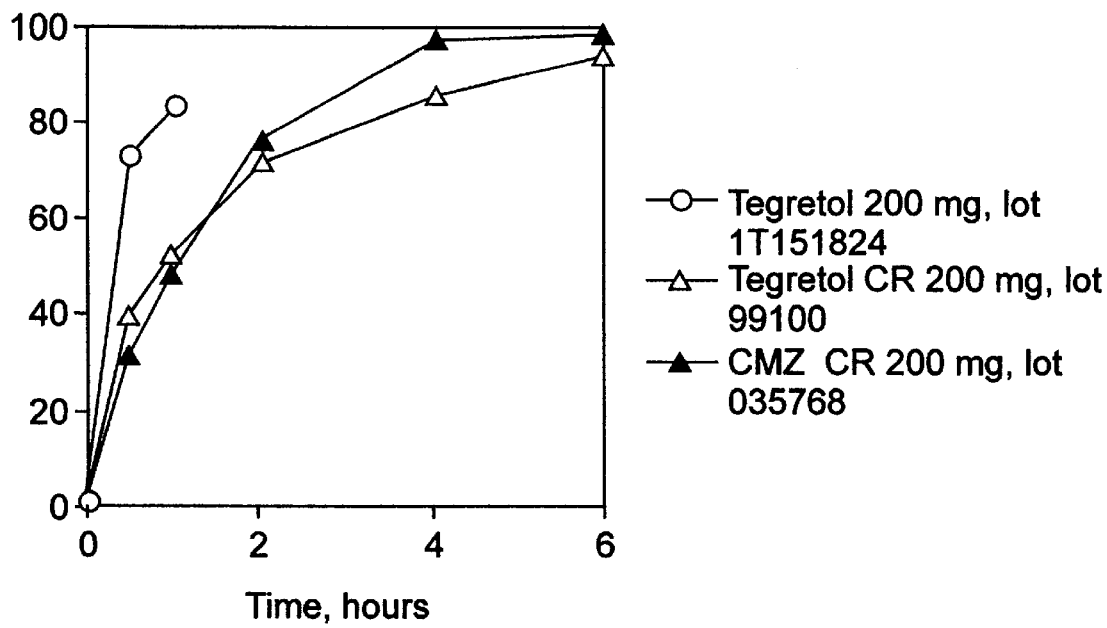
Fig. 1 Dissolution (%) of Carbamazepine (CMZ) tablets, 200 mg. 1% SLS, app. USP 2
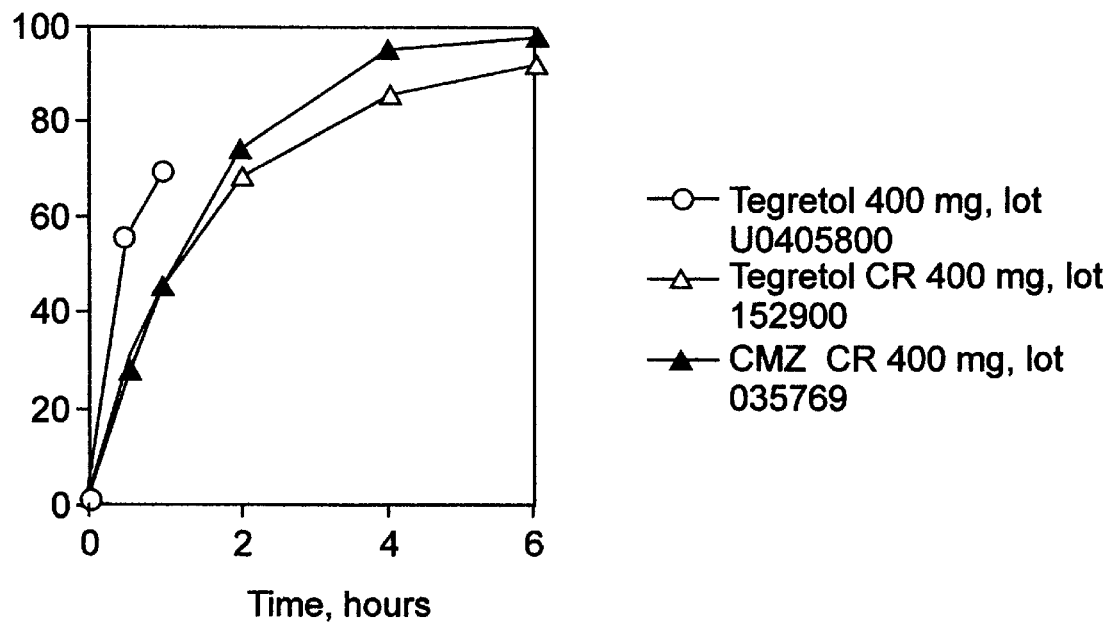
Fig. 2 Dissolution (%) of Carbamazepine (CMZ) tablets, 400 mg. 1% SLS, app. USP 2

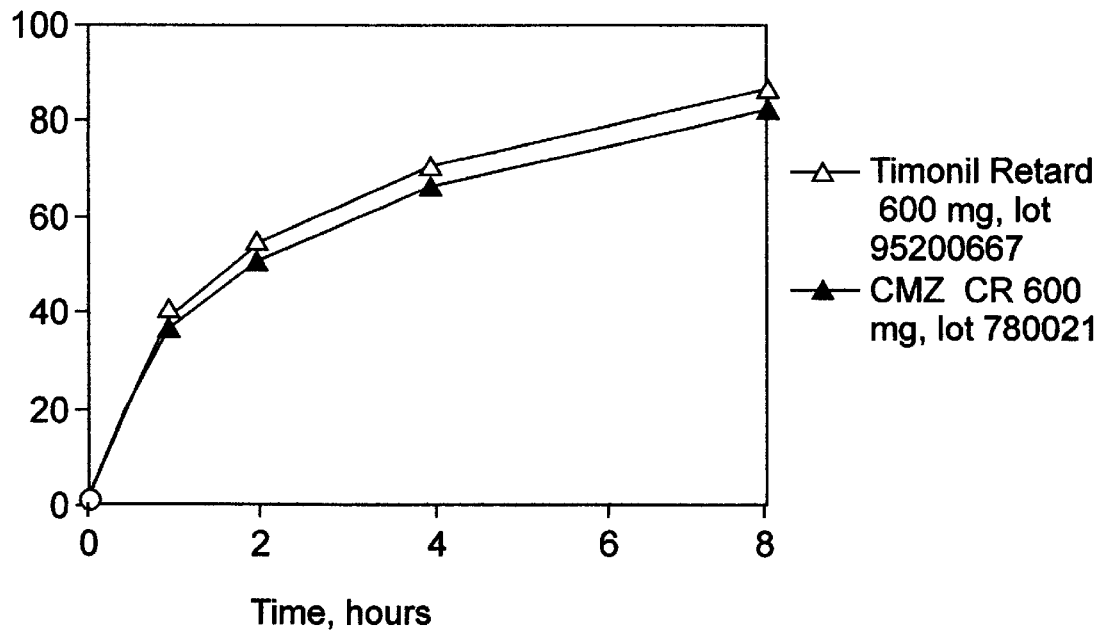
Fig. 3 Dissolution (%) of Carbamazepine (CMZ) tablets, 600 mg. 0.5% SLS, app. USP
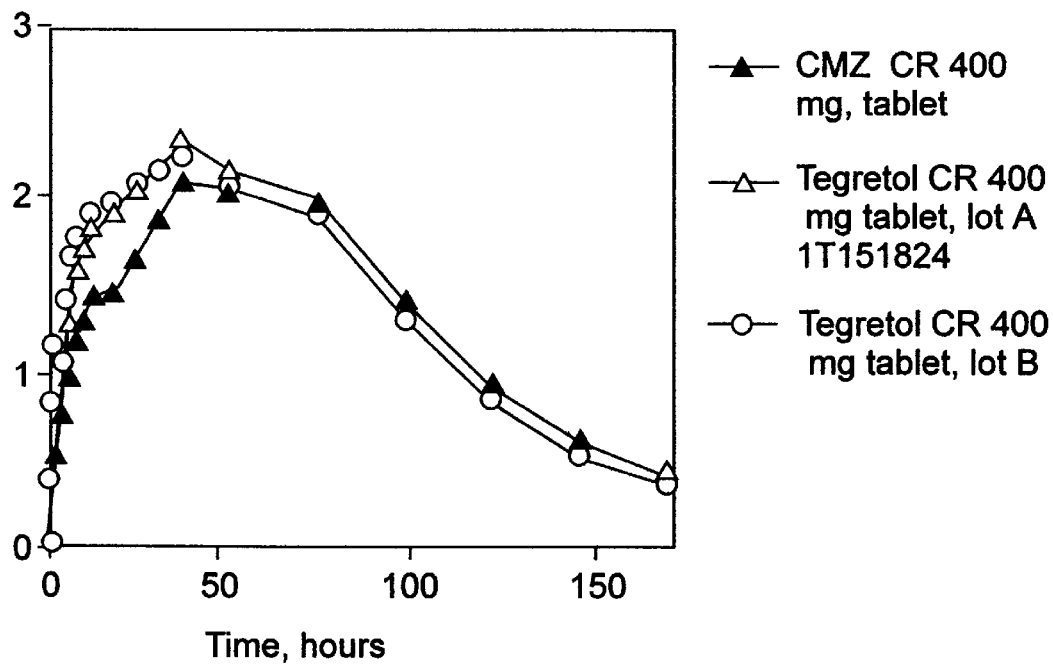
Fig. 4 Mean plasma carbamazepine (CMZ) concentrations (mg/L). Single dose, 400 mg, bioavailability study.

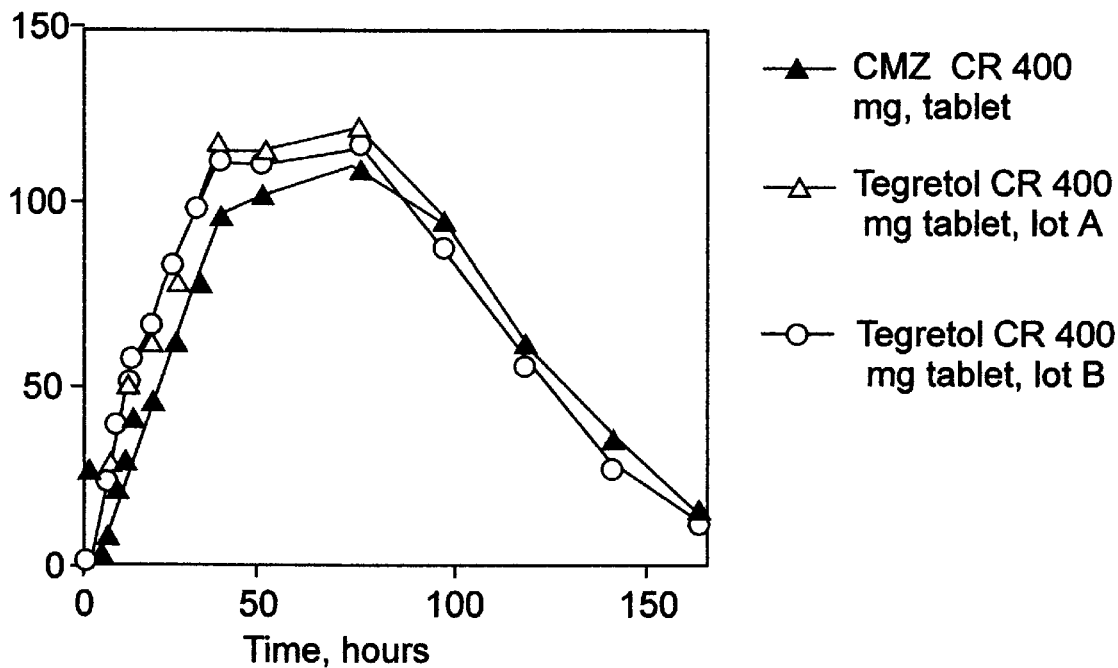
Fig. 5 Mean plasma carbamazepine metabolite CMZ -10,11-epoxide concentrations (ng/mL). Single dose, 400 mg, bioavailability study

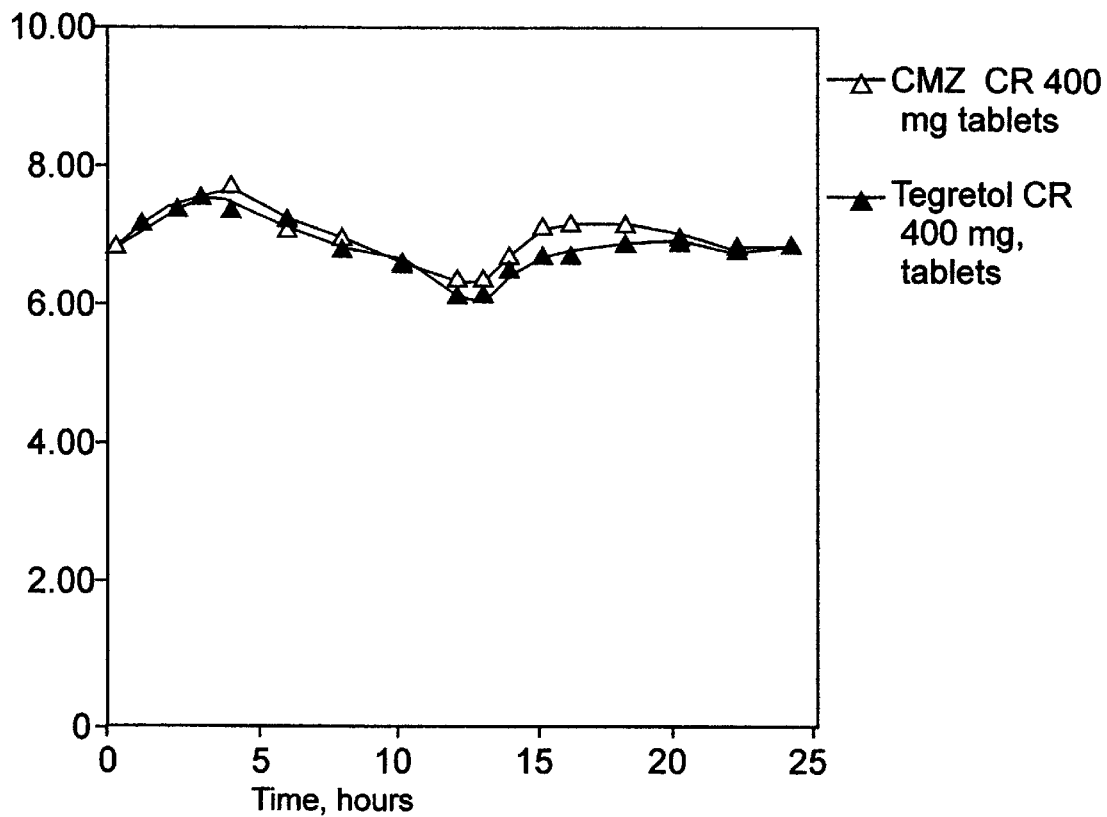
Fig. 6 Mean plasma carbamazepine (CMZ) concentrations (mg/L). Multiple dose, bioavailability study.

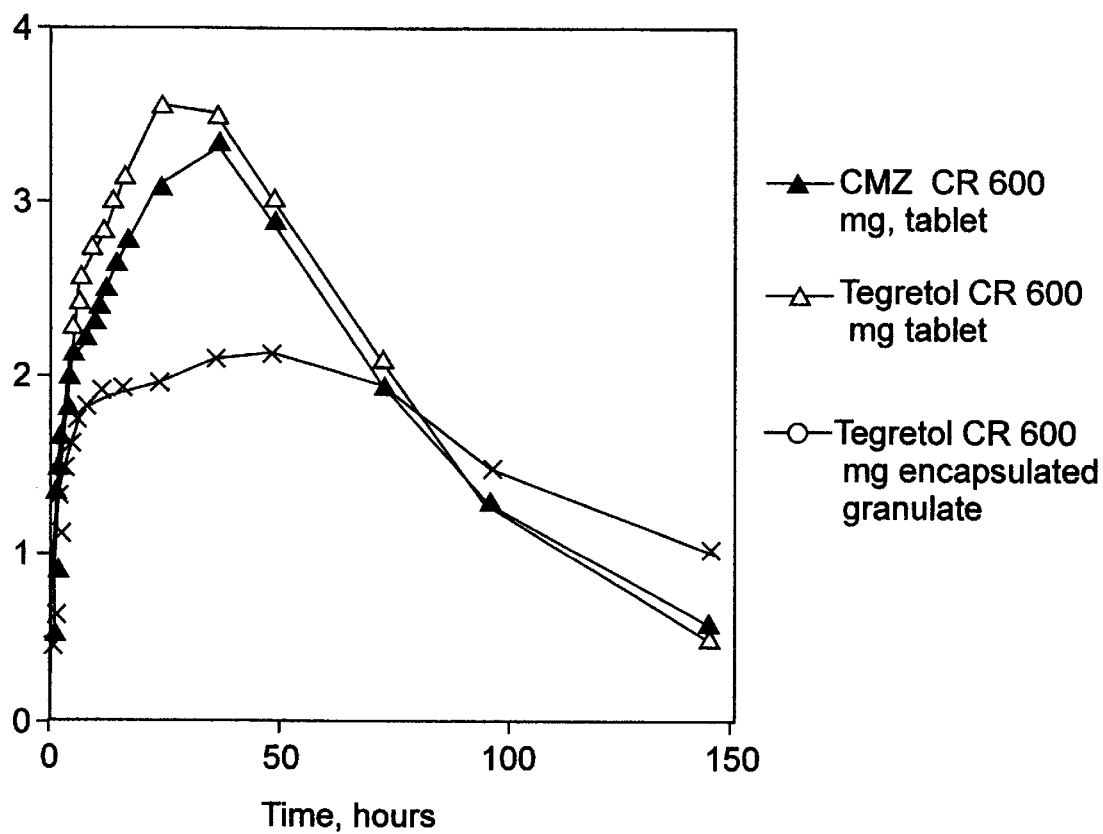
Fig. 7 Mean plasma carbamazepine (CMZ) concentrations (mg/L). Single dose, 600 mg, bioavailability study.

SUSTAINED RELEASE FORMULATION OF CARBAMAZEPINE

FIELD AND BACKGROUND OF THE INVENTION

The present invention relates to a sustained release pharmaceutical preparation in tablet form, where the active ingredient is an anti-convulsant medication, preferably carbamazepine.

Seizures caused by epilepsy require long-term therapy and most anti-epileptic medications must be administered several times a day[1]. Carbamazepine is used as an anti-convulsant medication in the treatment of epilepsy. Although carbamazepine (CMZ) has an initial half-life of 20–40 hrs, the half life becomes shorter through autoinduction during repetitive administration. Carbamazepine's half-life is decreased to 12 hrs with a single dose and 8 hrs upon multiple dose[2]. Therefore, sustained release formulations of these drugs have been developed. Carbamazepine is reported to be quite erratic in its absorption[3]. Possible reasons for irregular or inconsistent absorption are (a) low water solubility and physico-chemical properties of the molecule leading to very slow dissolution rate in the gastrointestinal fluid, (b) anticholinergic properties of the drug which may become more evident during prolonged treatment and thus modify its gastrointestinal transit time. Plasma $t_{max}$ is reported to be 4–8 hrs after oral administration, but may be delayed for more than 24 hrs. Plasma protein binding is about 75% and plasma levels of carbamazepine are variable ranging from 0.5 to 25 mcg/ml. Usual adult therapeutic levels are between 4–12 mcg/ml. The predominant pathway of metabolism involves conversion to carbamazepine 10,11-epoxide. This metabolite is as active pharmacologically as the parent compound and its concentration in plasma and brain may reach 50% of that of carbamazepine. The 10,11-epoxide further metabolizes to inactive compound, which is excreted in the urine.

A sustained release formulation, such as is provided by the present invention would smooth the fluctuations in plasma drug concentrations and diminish concentration related side effects of the drug, which is sometimes close to a daily dosage of up to 2000 mg.

German Patent No. 4423078 discloses a delayed-release oral dosage form of carbamazepine. The formulation disclosed differs significantly from the present invention. German Patent No. 4423078 discloses a tablet, containing water soluble plasticizers and a coating which contains talc. The formulation of the present invention is a disintegrating tablet, containing hydrophobic plasticizers and carbamazepine particles coated by a coating dispersion of a different quantitative composition and not containing talc.

Japanese Patent Application No. 94-298499 discloses a controlled release formulation of carbamazepine. However, the formulation disclosed is substantially different from the present invention. The formulation of the Japanese patent contains 3 coating layers, compared to the single coating layer of the present invention.

None of these prior art references suggested or disclosed the use of the combination of coating dispersion, hydrophobic plasticizer and disintegrating agent of the carbamazepine formulation of the present invention.

It would be highly advantageous to have, an effective sustained release carbamazepine formulation drug which is lower in cost and yet which is suitable for the treatment of seizures caused by epilepsy, as is described in the present invention.

SUMMARY OF THE INVENTION

The present invention provides a pharmaceutical preparation in tablet form, where the active ingredient is an anti-convulsant medication, preferably a sustained release formulation, and most preferably a sustained release formulation where the active ingredient is carbamazepine.

In a first embodiment the present invention provides a tablet for prolonged release of a medication, comprising (a) a pharmaceutically effective amount of carbamazepine particles; (b) a methacrylic polymer; and (c) additional excipients; wherein said methacrylic polymer and at least one additional excipient form a single coating layer over said carbamazepine particles and at least one additional excipient is present as an extragranular ingredient.

In a preferred embodiment the size of the carbamazepine particles is from about 30 mesh size to about 200 mesh size.

In a preferred embodiment the methacrylic polymer is selected from the group consisting of Eudragit RS, Eudragit RL, Eudragit RS30D or Eudragit RL30D aqueous dispersions, and mixtures thereof.

In a preferred embodiment the methacrylic polymer is present in an amount such that the dry weight ratio of methacrylic polymer to carbamazepine exceeds a ratio of about 0.11:1.

In a preferred embodiment the at least one additional excipient is selected from the group consisting of a diluent, a disintegrant and a lubricant.

In a preferred embodiment the diluent is selected from the group consisting of microcrystalline cellulose, lactose and mixtures thereof.

In a preferred embodiment the diluent is present in an amount of about 5% to about 30% of the, weight of the final tablet.

In a preferred embodiment the lubricant is selected from the group consisting of stearic acid and a salt thereof.

In a preferred embodiment the lubricant is present in an amount of from about 0.2% to about 1% of the weight of the final tablet.

In a preferred embodiment the route of administration is oral.

In a second embodiment, the present invention provides a tablet for prolonged release of a medication, comprising (a) a pharmaceutically effective amount of carbamazepine particles, (b) a methacrylic polymer and (c) at least one additional excipient, wherein the carbamazepine particles, the methacrylic polymer and the at least one additional excipient form a disintegrating tablet.

In a preferred embodiment the tablet farther comprises a disintegrant.

In a preferred embodiment the disintegrant is selected from the group consisting of starch, pregelatinized starch, sodium crosscarermellose and sodium starch glycolate.

In a preferred embodiment the starch is present in an amount of from about 2% to about 6% of the weight of the final tablet.

In a preferred embodiment the sodium starch glycolate is present in an amount of from about 0.8% to about 5% of the weight of the final tablet.

In a third embodiment, the present invention provides a tablet for prolonged release of a medication, comprising (a) a pharmaceutically effective amount of carbamazepine particles; (b) a methacrylic polymer; (c) a hydrophobic plasticizer; and (d) at least one additional excipient, wherein the methacrylic polymer and the hydrophobic plasticizer form a coating dispersion.

In a preferred embodiment the hydrophobic plasticizer is diethyl phthalate.

In a preferred embodiment the dry weight ratio of hydrophobic plasticizer to methacrylic polymer is in a range of from about 0.05:1 to about 0.3:1.

In a fourth embodiment the present invention provides a method of preparing a sustained release formulation of carbamazepine, comprising the steps of (a) forming a hydrophobic coating; (b) applying the hydrophobic coating dispersion onto carbamazepine particles to form coated granules; (c) blending disintegrating agents, diluents and lubricants with the granules to form a blend; and (d) compressing the blend to form a tablet.

In a preferred embodiment the coating dispersion comprises a hydrophobic plasticizer and a methacrylic polymer.

In a fifth embodiment the present invention provides a tablet for prolonged release of a medication, consisting essentially of (a) a pharmaceutically effective amount of carbamazepine particles, (b) a methacrylic polymer and (c) at least one additional excipient, wherein the methacrylic polymer and the at least one additional excipient form a single coating layer over the carbamazepine particles.

BRIEF DESCRIPTION OF THE DRAWINGS

Results of tests performed on tablets of the invention are herein described, by way of example only, with reference to the accompanying drawings, wherein:

FIG. 1 shows comparative dissolution profiles of Tegretol™ 200 mg, Tegretol™ Retard 200 mg and the 200 mg dosage of the formulation of the present invention;

FIG. 2 shows comparative dissolution profiles of Tegretol™ 400 mg, Tegretol™ Retard 400 mg and the 400 mg dosage of the formulation of the present invention;

FIG. 3 shows comparative dissolution profiles of Timonil Retard 600 mg and the formulation of the present invention as carbamazepine CR 600 mg tablets;

FIG. 4 shows mean plasma carbamazepine concentrations from the single 400 mg dose bioavailability study in fasted volunteers;

FIG. 5 shows mean plasma carbamazepine 10,11-epoxide concentrations from the single 400 mg dose comparative bioavailability study in fasted volunteers;

FIG. 6 shows mean plasma carbamazepine concentrations from the multiple dose comparative bioavailability study in fasting volunteers; and FIG. 7 shows mean plasma carbamazepine concentrations from the single 600 mg dose comparative bioavailability study in fasting volunteers.

DESCRIPTION OF THE PREFERRED EMBODIMENTS

The present invention provides a pharmaceutical preparation in tablet form, where the active ingredient is an anti-convulsant medication, preferably a sustained release formulation, and most preferably a sustained release formulation where the active ingredient is carbamazepine. The product is in tablet form and production is simplified by the procedure of the present invention.

The structure features a compressed core of particles or granules containing carbamazepine coated with delayed release coating materials, polymers and hydrophobic plasticizers, and at least one additional excipient. The additional excipients include pharmaceutical diluents, disintegrants and lubricants.

The delayed release coating materials (dissolution retarding agents) are preferably methacrylic polymers, more preferably Eudragit RS, Eudragit RL, an aqueous dispersion of Eudragit RS30D and an aqueous dispersion of RL30D and mixtures thereof, most preferably an aqueous dispersion of Eudragit RS30D (manufactured by Rohm Pharma, Germany). These polymers provide a uniform film with a pH-independent drug permeability, retard the dissolution rates and can be regulated in quantities with a proper optimized process to yield desired drug release characteristics. Preferably, the weight ratio of dry methacrylic polymer to carbamazepine exceeds 0.11:1 methacrylic polymer to carbamazepine.

Plasticizers are added to methacrylic polymer lacquers to enhance the plasticity of the lacquer film and to modify the sustained action of the polymer. The plasticizer is preferably a hydrophobic plasticizer and most preferably diethyl phthalate (DEP). Preferably, the weight ratio of diethyl phthalate to dry methacrylic polymer is in a range of from about 0.05:1 to about 0.3:1 and most preferably, the ratio of diethyl phthalate to dry methacrylic polymer is in a range of from about 0.015:1 to about 0.25:1.

The excipients give The desired flow of the granules, uniform compressibility into tablets and improve dissolution profiles. The pharmaceutical excipients include disintegrants, diluents and lubricants. Preferred disintegrants are starch, pregelatinized starch, sodium crosscaremellose and sodium starch glycolate. The disintegrants are preferably present in an amount of from about 2% to about 6% starch of the weight of the final tablet, or an amount of from about 0.8% to about 5% sodium starch glycolate of the weight of the final tablet. Preferred diluents include microcrystalline cellulose and lactose. More preferably, the lactose, the microcrystalline cellulose and mixtures thereof are present in an amount of from about 5% to about 30% weight per weight of the final tablet total weight. The lubricant is preferably magnesium stearate and most preferably is present in an amount of from about 0.2% to about 1.2% of the final tablet.

Although the following description will refer to the solid dosage form as a "tablet" for the sake of clarity, it should be understood that the present invention is not restricted to any one type or potency of tablet. For example, the present invention could also be in the form of tablets, troches or lozenges, with potencies of from about 100 mg to about 1000 mg of carbamazepine per dosage unit.

Optional ingredients include coloring and flavoring agents which are well known in the art. The tablet of the present invention is administered orally.

Formulations of carbamazepine are available in the background art, however the present invention provides a single layered coating over the carbamazepine particles and therefore is a product technically more convenient for manufacturing.

It is to be understood that the invention is not limited in its application to the details of construction and the arrangement of the components set forth in the following description. The invention includes other embodiments and can be practiced or implemented in various ways. Also it is to be understood that the phraseology and terminology employed herein is for the purpose of description only and should not be regarded as limiting.

EXAMPLES OF THE FORMULATIONS OF THE PRESENT INVENTION

The formulations of the present invention were prepared according a procedure which is generally described below, with adjustments to the amount and type of ingredients as specified in the Examples given below.

The first step of the procedure to produce the formulation of the present invention is preparation of granules formed and coated by application of a coating dispersion. A plasticizer is homogenized in water by use of a dispergating equipment. A dissolution retarding agent is then added and stirred to produce a coating dispersion. The carbamazepine is then sprayed on with the coating dispersion. A preferred particle size of carbamazepine is from about 30 mesh to about 200 mesh size. After spraying is finished, the granulate is dried slowly, until the moisture content of the granulate is in the specified range. The dried granulate is sized by being passed through a mill.

The next steps of the procedure are blending and compression. The granulate sub-lots are mixed in a blender. Disintegrants and diluents are passed through a suitable sieve. The sieved materials are added to the blend. A lubricant is then screened through a suitable sieve and added to the blend and mixed. The tablets are compressed with a rotary tabletting machine, equipped with punches specified for the product, and according to the specifications of the tablets.

The present invention may be better understood with reference to the Examples and the accompanying description. The formulation of each tablet is given below as a separate, illustrative Example.

Example 1

The 200 mg tablet of Example 1 was prepared from the following materials:

| Ingredient | Quantity (g) |
| --- | --- |
| carbamazepine | 200.0 |
| Eudragit RS30D (on dry basis) | 30.0 |
| diethyl phthalate | 4.5 |
| microcrystalline cellulose (Avicel PH101) | 40.0 |
| lactose monohydrous (100 mesh) | 42.5 |
| corn starch | 17.0 |
| sodium starch glycolate (Explotab) | 6.0 |
| magnesium stearate | 1.5 |

The method of preparation of this tablet formulation was as follows. Purified water and diethyl phthalate (4.5 g) were placed into a vessel, and diethyl phthalate was homogenized with an immersible dispergating tool. Eudragit RS30D (dispersions in an amount equal to 30 g on a dry basis) was added and stirred slowly. The weighed carbamazepine (200 g) was placed in a fluid bed apparatus and fluidizing was started. When the outlet temperature reached the established level, the solution was sprayed with the coating dispersion. After the spraying was finished, the granulate was dried slowly in the same apparatus by warming until the outlet air temperature reached the established level. The drying was stopped and the granulate's moisture was checked. The dried granulate was then passed through an oscillating mill and the moisture content checked.

The granulate was further mixed in a blender. Corn starch (17.0 g), microcrystalline cellulose (Avicel PH101; manufactured by FMC, USA; 40.0 g), lactose (42.5 g), and sodium starch glycolate (Explotab; manufactured by E. Mendel, USA; 6.0 g) were sieved and added to the blend mix. Magnesium stearate (1.5 g) was then screened and added to the blend and mixed. The tablets were then compressed with a rotary tabletting machine equipped with punches specific for the product.

Example 2

The 400 mg tablet of Example 2 was prepared from the following materials:

| Ingredient | Quantity (kg) |
| --- | --- |
| carbamazepine | 45.0 |
| Eudragit RS30D (on dry basis) | 6.75 |
| diethyl phthalate | 1.01 |
| microcrystalline cellulose (Avicel PH101) | 9.00 |
| lactose monohydrous (100 mesh) | 9.56 |
| corn starch | 3.825 |
| sodium starch glycolate (Explotab) | 1.35 |
| magnesium stearate | 0.34 |

The method of preparation of the formulation of Example 2 was the same as for Example 1.

Example 3

The 400 mg tablet of Example 3 was prepared as for Example 1, however instead of Eudragit RS30D (15% to carbamazepine weight), a mixture of Eudragit RS30D (12% to carbamazepine weight) and Eudragit RL30D (12% to carbamazepine weight) was used.

| Ingredient | mg/tablet |
| --- | --- |
| carbamazepine | 400.0 |
| Eudragit RS30D and Eudragit RL30D | 48.0 |
| diethyl phthalate | 4.8 |
| microcrystalline cellulose (Avicel PH101) | 80.0 |
| lactose monohydrous (100 mesh) | 85.0 |
| corn starch | 34.0 |
| sodium starch glycolate (Explotab) | 12.0 |
| magnesium stearate | 3.0 |

Example 4

| Ingredient | mg/tablet |
| --- | --- |
| carbamazepine | 600.0 |
| Eudragit RS30D (15%) (on a dry basis) | 90.0 |
| diethyl phthalate | 13.5 |
| microcrystalline cellulose (Avicel PH101) | 120.0 |
| lactose monohydrous (100 mesh) | 127.5 |
| corn starch | 51.0 |
| sodium starch glycolate (Explotab) | 18.0 |
| magnesium stearate | 4.5 |

The 600 mg tablet of Example 4 was prepared as for Example 1.

Example 5

| Ingredient | mg/tablet |
| --- | --- |
| carbamazepine | 400.0 |
| Eudragit RS30D (20%) on dry basis | 5.0 |
| diethyl phthalate (6.5%) | 9.0 |
| microcrystalline cellulose (Avicel PH101) | 80.0 |
| lactose monohydrous (100 mesh) | 85.0 |
| corn starch | 34.0 |
| sodium starch glycolate (Explotab) | 12.0 |
| magnesium stearate | 3.0 |

The 400 mg formulation of Example 5 was prepared as for Example 1, using Eudragit RS30D (20% to carbamazepine weight) and DEP (6.5% to Eudragit dry weight).

Example 6

| Ingredient | mg/tablet |
| --- | --- |
| carbamazepine | 400.0 |
| Eudragit RS30D (20%) on dry basis | 80.0 |
| diethyl phthalate (10%) | 8.0 |
| microcrystalline cellulose (Avicel PH101) | 80.0 |
| lactose monohydrous (100 mesh) | 85.0 |
| corn starch | 34.0 |
| sodium starch glycolate (Explotab) | 12.0 |
| magnesium stearate | 3.0 |

The 400 mg formulation of Example 6 was prepared as for Example 1, using Eudragit RS30D (20% to carbamazepine weight) and DEP (10% to Eudragit dry weight).

Example 7

| Ingredient | mg/tablet |
| --- | --- |
| carbamazepine | 400.0 |
| Eudragit RS30D (26%) on dry basis | 104.0 |
| diethyl phthalate (10%) | 10.4 |
| microcrystalline cellulose (Avicel PH101) | 80.0 |
| lactose monohydrous (100 mesh) | 85.0 |
| corn starch | 34.0 |
| sodium starch glycolate (Explotab) | 12.0 |
| magnesium stearate | 3.0 |

The 400 mg formulation of Example 7 was prepared as for Example 1, using Eudragit RS30D (26% to carbamazepine weight) and DEP (10% to Eudragit dry weight).

Example 8

| Ingredient | mg/tablet |
| --- | --- |
| carbamazepine in a mixture of Eudragit RS30D (15%) coated granules and Eudragit RS30D (26%) coated granules (on dry basis) containing also diethylphthalate (10% to Eudragit dry weight) | 400.0 |
| diethyl phthalate (10%) | 9.0 |
| microcrystalline cellulose (Avicel PH101) | 80.0 |
| lactose monohydrous (100 mesh) | 85.0 |
| corn starch | 34.0 |
| sodium starch glycolate (Explotab) | 12.0 |
| magnesium stearate | 3.0 |

The 400 mg formulation of Example 8 was prepared as for Example 1, using a mixture of Eudragit RS30D (15% of carbamazepine weight) coated granules and Eudragit RS30D (26% of carbamazepine weight) coated granules.

Example 9

| Ingredient | mg/tablet |
| --- | --- |
| carbamazepine | 200.0 |
| Eudragit RS30D (25%) on dry basis | 104.0 |
| diethyl phthalate (10%) | 10.4 |
| microcrystalline cellulose (Avicel PH101) | 40.0 |
| lactose monohydrous (100 mesh) | 42.5 |
| corn starch | 17.0 |
| sodium starch glycolate (Explotab) | 6.0 |
| magnesium stearate | 1.5 |

The 200 mg formulation of Example 9 was prepared as for Example 1, except Eudragit RS30D (52% of carbamazepine weight) and DEP (10% of Eudragit dry weight) was used.

Example 10

| Ingredient | mg/tablet |
| --- | --- |
| carbamazepine | 200.0 |
| Eudragit RS30D (26%) | 52.0 |
| diethyl phthalate (10%) | 5.2 |
| lactose monohydrous (100 mesh) | 82.5 |
| corn starch | 17.0 |
| sodium starch glycolate (Explotab) | 6.0 |
| magnesium stearate | 1.5 |

The 200 mg formulation of Example 10 was prepared as for Example 7, except lactose was used as a single diluent, instead of a mixture of lactose and Avicel.

EXAMPLES OF IN VITRO AND IN VIVO STUDIES WITH THE FORMULATIONS OF THE PRESENT INVENTION

The tablets of the present invention were evaluated by using the following dissolution tests and bioequivalence studies.

The dissolution test was performed in two different media, water with addition of SLS and water with 0.1N HCl. Along the transit through the gastrointestinal tract, any modified release dosage form contacts body fluids at various pH levels. In the stomach under fasting conditions the pH is acidic. Under the buffering influence of chyme, the pH in the stomach can rise to an average of about pH 5 or even above. In the intestine under the influence of bile and pancreatic juices, the pH level rises to the physiological neutral point of about pH 7.4 and to an even more alkaline pH 8. Therefore, dissolution tests were performed at various pH media within the physiological range. To model the influence of surface active physiological ingredients that naturally occur in the digestive fluids, sodium lauryl sulfate or a polysorbate are added to the dissolution media. This procedure is also necessary if the drug under investigation is a poorly wettable drug, such as carbamazepine.

Comparative dissolution profiles are shown in FIGS. 1–3. FIG. 1 shows comparative dissolution profiles of Tegretol™ 200 mg, Tegretol™ Retard 200 mg and the 200 mg dosage of the formulation of the present invention. FIG. 2 shows comparative dissolution profiles of Tegretol™ 400 mg, Tegretol™ Retard 400 mg and the 400 mg dosage of the formulation of the present invention. FIG. 3 shows comparative dissolution profiles of Timonil Retard 600 mg and the formulation of the present invention as carbamazepine CR 600 mg tablets.

A number of bioequivalence studies were conducted comparing the 400 mg tablets of the formulation of the present invention as prepared according to Example 2, and the 600 mg tablets of the formulation of the present invention as prepared according to Example 4, with the originator's products, Tegretol™ Retard 400 mg tablets (trademark to Ciba-Geigy; Tegretol™ is the trade-name for the carbamazepine formulation), also known as Tegretol™ CR 400 in some countries, and Timonil Retard 600 mg (Desitin™). All studies are equally applicable to the 200 mg strength, since the 200 mg, 400 mg and 600 mg strengths are tabletted from a common final blend (proportional compositions for the finished product and equivalent manufacturing processes) and demonstrate comparable in vitro dissolution profiles.

These bioequivalence studies show that the formulation of the present invention is an effective formulation for a sustained release dosage of carbamazepine, and that the efficacy of this formulation is comparable to that of the originator's formulation.

Example 1
Single Dose Bioequivalence Study in Fasted Volunteers

This study was an open-label, single-dose, randomized, three-way crossover study with a 21-day washout between doses. The three formulations compared were the 400 mg tablet of the formulation of the present invention (treatment A), and samples of two different lots of Tegretol™ controlled release 400 mg formulation (manufactured by Ciba-Geigy—treatments B and C).

In total, 36 non-smoking, healthy male volunteers (aged 20–55 years and within ±15% of ideal body weight) entered the study. Thirty-four subjects completed the study. Subjects fasted for 10 hours before dosing and for four hours after dosing; standardized meals were provided thereafter.

Blood samples were collected at the following times: pre-dose and 1, 2, 3, 4, 6, 8, 10, 12, 18, 24, 30, 36, 48, 72, 96, 120, 144 and 168 hours after dosing. Plasma samples were analyzed for carbamazepine and carbamazepine 10,11-epoxide concentrations using a validated HPLC method. The results of the pharmacokinetic analyses are shown in FIGS. 4 and 5.

Under the single dose fasting conditions of this study, the formulation of the tablets of the present invention and Tegretol™ CR 400 mg were bioequivalent, having comparative rates of absorption and comparative extent of absorption. The ratio of mean plasma concentrations for the formulation of the present invention to Tegretol™ CR 400 mg tablets, lot A, was 95%, 96% and 95% for $AUC_{0-t}$, AUC and Cmax respectively. In comparison to Tegretol™ CR 400 mg tablets, lot B, these values were 100%, 100% and 97%, respectively.

The confidence intervals for the log-transformed data were 89.2% to 99.5% for $AUC_{0-t}$, 89.9% to 100.3% for AUC, and 89.1% to 96.7% for Cmax in relation to lot A. These intervals were 93.4% to 104.2%, 93.9% to 104.7% and 91.0% to 100.8%, respectively, for lot B.

The 90% confidence intervals for all of the above parameters were within the range of 80% to 120% for the observed data and within the range of 80% to 125% for the log-transformed data.

Similar results were also obtained when analyzing the plasma concentration curves for the metabolite carbamazepine 10,11-epoxide.

The formulation of the present invention was therefore, found to be bioequivalent to Tegretol™ controlled release 400 mg formulation (manufactured by Ciba-Geigy). Thus, the formulation of the present invention is clearly suitable and effective for the oral administration of carbamazepine.

Example 2
Multiple Dose Bioequivalence Study in Fasting Volunteers

This study was an open-label, multiple-dose, randomized, two-way crossover comparison of 400 mg tablet of the formulation of the present invention and Tegretol™ controlled release 400 mg tablet (manufactured by Ciba-Geigy).

Subjects first entered a pre-treatment phase in which Tegretol™ controlled release 400 mg tablets were administered at a dose of 200 mg (half a tablet) twice daily for four days followed by 400 mg (one tablet) twice daily for 3 days (14 doses in total). This pre-treatment phase was undertaken to assess the safety of multiple doses of carbamazepine in volunteers and to reduce the between-period differences in baseline metabolic status.

The washout periods between the pre-treatment phase and the first period of the crossover study, and between the two treatment periods, were at least 12 hours, in order to maintain steady state conditions. The dosage regimen used during the crossover study was 400 mg twice daily for 8 days (16 doses).

In total, 24 non-smoking, healthy male volunteers (aged 24–53 years and within ±15 % of ideal body weight) were enrolled and 22 completed the study. On day 8 of each period, subjects fasted for at least 10 hours before and 4 hours after the morning dose and for about 3 hours before and after the evening dose.

Blood samples were collected prior to the first dose of the pre-treatment phase and prior to the morning dose on days 6, 7 and 8 of each test period. Samples were collected 1, 2, 3, 4, 6, 8, 10, 12 (prior to the evening dose), 13, 14, 15, 16, 18, 20, 22 and 24 hours after the morning dose on day 8 of each test period. Plasma samples were analyzed for carbamazepine and carbamazepine 10,11-epoxide concentrations using a validated HPLC method.

The results of the pharmacokinetic analyses are shown in FIG. 6. The results for Cmin on days 6, 7 and 8 confirmed that steady state had been reached.

The data presented in the table in FIG. 6 and corresponding data adjusted for potency showed that the 95% confidence interval limits were well within the range 80–125% for $AUC_{0-12}$, $AUC_{12-24}$, $Cmax_{0-12}$, $Cmax_{12-24}$, $Cmin_{0-12}$ and $Cmin_{12-24}$ for both carbamazepine and its 10,11-epoxide. The results wore similar for log (ln) transformed data.

The study showed that the formulation of the present invention and the reference 400 mg controlled release carbamazepine tablets (Ciba-Geigy) were bioequivalent under steady state conditions.

Example 3
Comparative Pharmacokinetic Analysis of Two Sustained Release Formulations of Carbamazepine 600 mg The study was aimed at determining the bioequivalence of the formulation of the present invention as a carbamazepine 600 mg sustained release tablet with Desitin™ carbamazepine 600 mg tablet (Timonil 600 Retard) under single dose fasting conditions. A secondary objective was to determine the bioavailability of capsules filled with granules, rather than compressed into the final tablet dosage form.

Study Design

The study was a single dose, randomized 3-way crossover bioequivalence study in fasting, healthy volunteers. Three treatments A, B and C were tested. Treatment A was the carbamazepine 600 mg sustained release tablet formulation of the present invention. Treatment B contained the reference treatment, Desitin™ carbamazepine 600 mg sustained release tablets (Timonil 600 Retard) and treatment C was the carbamazepine 600 mg granulate of Taro Ltd. A single oral dose of 600 mg was given with 2 glasses of water between 7.00 a.m. and 8.00 a.m. of each dosing day. A total of 19 male volunteers were enrolled allowing for one dropout. All volunteers completed the study. Samples from all volunteers were analyzed.

The nineteen volunteers were non-smokers and ranged in age from 19 to 27 years (mean±SD=24±3 years) with all average weight of 75±15 kg. The volunteers were selected on the basis of a negative medical history with no drug abuse, no heart conduction system problems, a normal physical examination and normal (routine) biochemical, hematolgical blood and urine analyses. The biochemical and hematological analyses were also repeated at the end of each phase of the study.

Each subject received at separate times 1×600 mg carbamazepine in one of the tested the sustained release formulations:

The administration of the three carbamazepine formulations was conducted in a randomized crossover design, with an interval of two weeks between dosing sessions. The subjects fasted 12 hours before dosing and for 5 hours after dosing. Standard lunch and dinner were served at 5 hours and 12 hours respectively after dosing. Water was permitted ad lib 2 hours after dosing.

Samples (each 8 ml) were collected into heparinized vacutainer tubes via an indwelling peripheral catheter before dosing and at 1, 2, 3, 4, 5, 6, 7, 8, 9, 10, 12, 14 and 16 hours after dosing; and by venipuncture at 24, 36, 48, 72, 96 and 144 hours after dosing. Subjects arrived at the study site one hour before dosing and remained there until after the 16-hour blood draw. The subjects then returned to the study site 24, 36, 48, 72, 96 and 144 hours after dosing for blood draws. There was a washout period of two weeks (14 days) between doses. Results are shown in FIG. 7.

Plasma carbamazepine concentration was measured using the following validated and specific HPLC assay method. The pharmacokinetic parameters calculated were $AUC_{0-t}$, AUC, Cmax, tmax, MRT and $t_{1/2}$. Analysis of variance (ANOVA) and confidence interval tests were conducted in order to compare the $AUC_{0-t}$, AUC, Cmax and MRT.

Analysis of variance showed no period or sequence effect in the calculation of AUC, Cmax and MRT values (p<0.05) of carbamazepine 600 mg sustained release tablet formulation of the present invention and granules filled into capsules relative to Timonil 600 Retard. The mean values of these three parameters for the formulation of tablets of the present invention were well within the acceptable confidence interval of 80–125%.

Under the single dose fasting conditions of this study, the formulation of the tablets of the present invention and Timonil 600 Retard were bioequivalent, having comparable rates and extents of absorption. The ratio of means of the formulation of the present invention to Timonil 600 Retard was 96, 97, 91 and 108% for $AUC_{0-t}$, AUC, Cmax and MRT respectively. The mean values were well within the acceptable confidence intervals of 80–125%.

The confidence intervals for the log-transformed data were 88.6% to 101.8% for $AUC_{0-t}$; 89.9% to 103.1% for AUC; 84.7% to 96.3% for Cmax; and 102.2% to 110.9% for MRT. The ratios of geometric means were 95, 96, 90 and 106% for $AUC_{0-t}$, AUC, Cmax and MRT respectively. The mean values were well within the acceptable confidence intervals of 80–125%.

The 90% confidence intervals for all the above parameters were within the 80–120% for the observed data and were within the 80–125% range for the log-transformed data.

Under the single dose fasting conditions of this study, the encapsulated preparation and the Timonil 600 Retard formulations had different rates and extents of absorption. The tablet formulation of the present invention and Timonil 600 Retard were found to have comparable rates and extents of absorption under fasting conditions and thus were found to be bioequivalent.

It will be appreciated that the above examples and descriptions are intended only to serve as examples, and that many other embodiments are possible within the spirit and the scope of the present invention.

REFERENCES CITED

1. Porter R. J. Antiepileptic drug, $3^{rd}$ edition, pp 117–131, Raven Press, New York 1989.
2. Sustained release formulations of antiepileptics. Clin. Pharmacokinet. 22, (1), 1992, p. 11–21.
3. Morsells, P. L. Carbamazepine absorption, distribution and excretion. In Levy et al (Eds) Antiepileptic drugs, $3_{rd}$ edition, pp. 473–490, Raven Press New York, 1989.

What is claimed is:

1. A tablet for prolonged release of a medication, comprising:
   (a) a pharmaceutically effective amount of carbamazepine particles;
   (b) a methacrylic polymer; and
   (c) additional excipients;
   wherein said methacrylic polymer and at least one additional excipient form a single coating layer over said carbamazepine particles and at least one additional excipient is present as an extragranular ingredient.

2. The tablet of claim 1, wherein the size of said carbamazepine particles is from about 30 mesh size to about 200 mesh size.

3. The tablet of claim 1, wherein said methacrylic polymer is selected from the group consisting of, Poly (ethyl acrylate, methyl methacrylate, trimethylammonioethyl methacrylic chloride) (1:2:0.1), Poly (ethyl acrylate, methyl methacrylate, trimethylammonioethyl methacrylic chloride) (1:2:0.2), aqueous dispersions containing about 30% of Poly (ethyl acrylate, methyl methacrylate, trimethylammonioethyl methacrylic chloride) (1:2:0.1), or aqueous dispersions containing about 30% of Poly (ethyl acrylate, methyl methacrylate, trimethylammonioethyl methacrylic chloride) (1:2:0.2) and mixtures thereof.

4. The tablet of claim 1, wherein said methacrylic polymer is present in an amount exceeding dry methacrylic polymer to carbamazepine weight ratio of from about 0.11:1 methacrylic polymer to carbamazepine.

5. The tablet of claim 1, wherein said at least one additional extragranular excipient is selected from the group consisting of a diluent, a disintegrant and a lubricant.

6. The tablet of claim 5, wherein said diluent is selected from the group consisting of microcrystalline cellulose and lactose, and a mixture thereof.

7. The tablet of claim 5, wherein said diluent is present in an amount of about 5% to about 30% of the weight of the final tablet.

8. The tablet of claim 5, wherein said lubricant is magnesium stearate.

9. The tablet of claim 5, wherein said lubricant is present in an amount of from about 0.2% to about 1.2% of the weight of the final tablet.

10. The tablet of claim 1, wherein the route of administration is oral.

11. A tablet for prolonged release of a medication, comprising:
   (a) a pharmaceutically effective amount of carbamazepine particles;
   (b) a methacrylic polymer;
   (c) a hydrophobic plasticizer; and
   (d) at least one additional excipient;
wherein said carbamazepine particles, said methacrylic polymer and said at least one additional excipient form a disintegrating tablet.

12. The tablet of claim 11, further comprising a disintegrant.

13. The tablet of claim 12, wherein said disintegrant is selected from the group consisting of starch, pregelatinized starch, sodium crosscaremellose and sodium starch glycolate.

14. The tablet of claim 12, wherein said starch is present in an amount of from about 2% to about 6% of the weight of the final tablet.

15. The tablet of claim 13, wherein said sodium starch glycolate is present in an amount of from about 0.8% to about 5% of the weight of the final tablet.

16. A tablet for prolonged release of a medication, comprising:
   (a) a pharmaceutically effective amount of carbamazepine particles;
   (b) a methacrylic polymer;
   (c) a hydrophobic plasticizer; and
   (c) at least one additional excipient;
wherein said methacrylic polymer and said hydrophobic plasticizer form a coating layer.

17. The tablet of claim 16, wherein said hydrophobic plasticizer is diethyl phthalate.

18. The tablet of claim 16, wherein said hydrophobic plasticizer is present in a weight ratio to said dry methacrylic polymer in a range of from about 0.05:1 to about 0.3:1.

19. The tablet of claim 16, wherein said hydrophobic plasticizer is present in a weight ratio to said methacrylic polymer in a range of from about 0.075:1 to about 0.25:1.

20. A method of preparing a sustained release formulation of carbamazepine, comprising the steps of:
   (a) forming a hydrophobic coating dispersion;
   (b) applying said hydrophobic coating dispersion onto carbamazepine particles to form coated granules;
   (c) blending disintegrating agents, diluents and lubricants with said granules to form a blend; and
   (d) compressing said blend to form a tablet.

21. The method of claim 20, wherein said coating dispersion comprises a hydrophobic plasticizer and a methacrylic polymer.

22. A tablet for prolonged release of a medication, consisting essentially of:
   (a) a pharmaceutically effective amount of carbamazepine particles;
   (b) a methacrylic polymer; and
   (c) at least one additional excipient;
wherein said methacrylic polymer and said at least one additional excipient form a single coating layer over said carbamazepine particles.

* * * * *